United States Patent
Cremonese et al.

(10) Patent No.: US 6,539,328 B1
(45) Date of Patent: Mar. 25, 2003

(54) DEVICE AND PROCESS FOR MEASUREMENT AND TREATMENT OF SPINAL MOBILITY

(75) Inventors: Joseph G. Cremonese, Greensburg, PA (US); Tamas Becse, Mars, PA (US); John B. Crunick, Moon Township, Allegheny County, PA (US); Lou L. Laskey, Jr., Cranberry, PA (US)

(73) Assignee: Sigma Instruments, Inc., Cranberry, PA (US)

(*) Notice: Subject to any disclaimer, the term of this patent is extended or adjusted under 35 U.S.C. 154(b) by 0 days.

(21) Appl. No.: 09/303,059

(22) Filed: Apr. 30, 1999

(51) Int. Cl.$^7$ .................... G01C 9/00; G01C 17/00
(52) U.S. Cl. .................................................. 702/151
(58) Field of Search ................. 702/42, 38, 41–36, 702/33–35, 113, 115, 124, 139, 150, 154, 151, 168, 183, 189; 600/594, 595, 553; 606/237, 238, 239

(56) References Cited

U.S. PATENT DOCUMENTS

| | | |
|---|---|---|
| 3,020,639 A | 2/1962 | Karpovich et al. |
| 3,258,007 A | 6/1966 | Karpovich et al. |
| 4,436,099 A | 3/1984 | Raftopoulos |
| 4,444,204 A | 4/1984 | Bryant et al. |
| 4,485,825 A | 12/1984 | Domjan et al. |
| 4,649,934 A | 3/1987 | Fraser et al. |
| 4,667,685 A | 5/1987 | Fine |
| 4,800,897 A | 1/1989 | Nilsson |
| 4,841,955 A | 6/1989 | Evans et al. |
| 4,883,069 A | 11/1989 | McLeod |
| 4,928,709 A | 5/1990 | Allison et al. |
| 5,188,121 A | 2/1993 | Hanson |
| 5,327,907 A | 7/1994 | Fischer |
| 5,373,858 A | 12/1994 | Rose et al. |
| 5,474,088 A | 12/1995 | Zaharkin et al. |
| 5,588,444 A | 12/1996 | Petragallo |
| 5,647,375 A * | 7/1997 | Farfan de los Godos ... 600/549 |
| 5,666,122 A * | 9/1997 | Evans .......................... 600/594 |
| 5,754,121 A | 5/1998 | Ward et al. |
| 5,758,658 A | 6/1998 | Petragallo |
| 5,772,610 A | 6/1998 | McGorry et al. |
| 5,897,510 A * | 4/1999 | Keller et al. ................. 600/594 |

* cited by examiner

*Primary Examiner*—John S. Hilten
*Assistant Examiner*—Demetrius Pretlow
(74) *Attorney, Agent, or Firm*—Thorpe Reed & Armstrong, LLP

(57) ABSTRACT

A device and process for measurement and treatment of spinal mobility is disclosed. The device includes an impulse and sensing head capable of determining spinal segment mobility by applying a force impulse to a spinal segment and generating a waveform characteristic of spinal mobility. An inclinometer disposed within the head determines the angle of incidence of the head in contact with the spinal segment in at least one, preferably three, axis. Characteristics of the waveform and the angle of incidence are analyzed to determine spinal mobility. The information in the waveform and device are then used to treat the patient by applying an oscillating head to a spinal segment so that spinal mobility is increased.

38 Claims, 11 Drawing Sheets

|  | PEAK 1 | PEAK 2 | PT1 | PT2 | RT1 | RT2 | FT1 | FT2 | FREQ 1 | FREQ 2 | PA% 1 | PA% 2 |
|---|---|---|---|---|---|---|---|---|---|---|---|---|
| C1A | 30.1 | 39.9 | 3.68 | 3.92 | 1.92 | 2.57 | 3.41 | 2.79 | 49.6 | 47.4 | 37.57 | 49.12 |
| C1B | 24.8 | 39.9 | 4.33 | 4.29 | 2.35 | 2.27 | 3.12 | 3.20 | 51.0 | 56.3 | 48.22 | 49.26 |
| C2 | 36.9 | 30.0 | 4.08 | 4.90 | 1.99 | 3.07 | 2.76 | 3.09 | 48.4 | 50.2 | 40.05 | 49.33 |
| C3 | 36.0 | 20.0 | 3.84 | 4.67 | 1.83 | 2.99 | 2.09 | 3.37 | 63.7 | 51.42 | 49.92 | 46.75 |
| C4 | 20.9 | 20.0 | 4.55 | 4.57 | 2.17 | 2.10 | 3.16 | 3.15 | 51.8 | 51.3 | 47.13 | 47.22 |
| C5 | 35.7 | 20.1 | 3.86 | 4.11 | 1.85 | 2.16 | 2.37 | 2.99 | 55.8 | 57.9 | 44.75 | 44.99 |
| C6 | 37.5 | 21.7 | 3.79 | 4.45 | 2.01 | 3.00 | 3.36 | 3.01 | 53.9 | 55.07 | 41.03 | 49.14 |
| C7 | 40.0 | 39.1 | 3.55 | 4.16 | 1.97 | 2.91 | 2.19 | 3.10 | 58.0 | 57.3 | 42.23 | 48.01 |
| T1 | 38.0 | 38.0 | 4.02 | 3.99 | 3.05 | 3.04 | 3.85 | 3.80 | 55.40 | 57.24 | 45.00 | 45.99 |
| T2 | 20.8 | 37.1 | 3.71 | 3.60 | 2.10 | 2.91 | 3.88 | 3.80 | 58.01 | 58.21 | 43.66 | 43.70 |
| T3 | 40.0 | 37.7 | 2.95 | 3.24 | 2.11 | 2.40 | 3.45 | 3.20 | 67.73 | 64.00 | 40.11 | 41.70 |
| T4 | 40.0 | 37.6 | 2.73 | 3.15 | 2.30 | 2.74 | 3.04 | 3.08 | 82.30 | 74.46 | 45.10 | 47.12 |
| T5 | 39.8 | 38.1 | 3.00 | 3.07 | 2.04 | 2.10 | 3.09 | 3.20 | 71.85 | 71.66 | 44.55 | 44.19 |
| T6 | 40.0 | 36.3 | 3.03 | 3.10 | 2.05 | 2.01 | 3.03 | 3.00 | 66.91 | 69.15 | 40.60 | 43.25 |
| T7 | 40.0 | 36.9 | 3.12 | 3.19 | 2.34 | 2.45 | 3.08 | 3.05 | 69.57 | 69.98 | 45.25 | 47.10 |
| T8 | 40.0 | 39.7 | 3.19 | 2.99 | 2.06 | 2.67 | 3.05 | 3.01 | 72.41 | 72.45 | 46.80 | 47.00 |
| T9 | 39.9 | 38.1 | 2.67 | 3.23 | 2.00 | 2.35 | 3.42 | 3.61 | 83.06 | 75.28 | 46.05 | 45.82 |
| T10 | 39.9 | 37.1 | 3.11 | 3.23 | 2.15 | 2.17 | 3.73 | 3.53 | 69.32 | 68.96 | 43.90 | 45.07 |
| T11 | 40.0 | 36.5 | 3.12 | 3.22 | 2.21 | 2.19 | 3.26 | 3.41 | 72.29 | 75.83 | 45.95 | 46.15 |
| T12 | 36.5 | 35.6 | 3.04 | 3.09 | 2.33 | 2.45 | 3.55 | 3.59 | 75.83 | 74.60 | 46.75 | 47.22 |
| L1 | 40.0 | 38.4 | 2.62 | 3.40 | 1.95 | 2.66 | 3.95 | 3.90 | 75.86 | 59.56 | 40.20 | 48.70 |
| L2 | 39.6 | 39.1 | 3.09 | 3.16 | 2.10 | 3.21 | 4.05 | 3.67 | 51.98 | 57.29 | 32.25 | 37.10 |
| L3 | 38.0 | 37.0 | 3.10 | 3.40 | 2.31 | 2.55 | 4.00 | 4.10 | 53.79 | 50.29 | 33.95 | 34.55 |
| L4 | 44.5 | 23.7 | 3.20 | 3.90 | 3.75 | 3.95 | 4.13 | 4.20 | 67.03 | 57.18 | 40.30 | 45.53 |
| L5 | 30.2 | 37.8 | 3.60 | 3.75 | 2.85 | 2.67 | 3.66 | 3.60 | 62.78 | 60.33 | 45.80 | 46.00 |
| S1 | 70.5 | 40.0 | 3.44 | 3.45 | 3.80 | 3.40 | 4.53 | 4.20 | 64.59 | 65.13 | 44.49 | 45.06 |
| S2 | 40.0 | 39.5 | 3.41 | 3.42 | 2.97 | 3.05 | 3.76 | 3.74 | 67.43 | 67.54 | 46.28 | 46.38 |
| S3 | 30.1 | 30.0 | 3.55 | 3.56 | 3.05 | 3.21 | 3.95 | 3.87 | 65.78 | 66.01 | 46.95 | 47.22 |
| S4 | 32.0 | 28.9 | 3.40 | 3.49 | 3.20 | 3.27 | 3.85 | 3.95 | 68.02 | 67.91 | 46.99 | 47.60 |
| S5 | 22.2 | 27.8 | 3.33 | 3.39 | 3.34 | 3.76 | 3.99 | 4.10 | 70.87 | 69.92 | 47.90 | 48.05 |

*Fig. 8*

DEVICE AND PROCESS FOR MEASUREMENT AND TREATMENT OF SPINAL MOBILITY

BACKGROUND OF THE INVENTION

1. Field of the Invention

This invention relates to a device for the computerized analysis of human spinal segment mobility which includes an inclinometer disposed within a piezoelectric impulse and sensing head so that the angle of incidence of the apparatus on the spine can be measured as spinal mobility is measured and a process for interpreting the characteristics of a wave form generated from the piezoelectric sensor which is in contact with the spinal segment while an impulse is applied to the segment.

2. Description of Prior Art

A spinal "motion segment" may be defined as two adjacent vertebrae, the intervertebral disc residing between and connected to the two adjacent vertebral segments, the collateral and capsular connective tissue, proximate musculature, and the fascia and integument, all associated with the motion segment. The sensing and measuring of joint mobility of human spinal segments has been described by many practitioners skilled in the art as manually and subjectively determining spinal segment mobility relative to a written standard as well as adjacent spinal segments. In the early art form, developed by practitioners of physical manipulation of spinal segments, the practitioner would manually stabilize the spinal segments superior and inferior to the segment selected for testing of a patient who was lying on a therapy table or sitting in an erect position. While the adjacent segments were so stabilized, the integument over the spinal segment to be tested would be grasped between the thumb and forefinger of the practitioner so that the spinous process of the segment in question would be trapped within the patient's integument and between the thumb and forefinger of the practitioner. The practitioner would then attempt to move the segment, using the spinous process as a lever, and at the same time make a mental observation and comparison to a reference determined by a written standard and experience and practice on many subjects. The observations would be graded and recorded by the practitioner. Intensive professional training is required to be able to sense and grade the amount of mobility or "stiffness" of each spinal segment. Grading mobility is an art form and while one practitioner might consistently grade the mobility with a reasonable amount of accuracy and precision, additional practitioners might disagree with the mobility grading of the first practitioner. Therefore, the accuracy of the grading varied with the experience and interpretive skills of individual practitioners.

Several years ago, laboratory devices were constructed so that a subject could be positioned reproducibly on a therapy table and a lever operated transducer would be applied to the spinal segment in question and moved through a given range of motion so that the energy required to move the segment was recorded and correlated to some chosen reference standard. This method was more objective but not practical for routine practice.

In 1992, a device for testing mobility and resistance of a spinal segment was invented. The device was comprised of a piezoelectric sensor that could be positioned in series with a spinal segment where a fixed pressure could be applied through the transducer so that the integument over the segment would be compressed by a known and reproducible amount. When the required compression was achieved, a cylindrical shaped metallic body, would be accelerated to impact the side of the piezoelectric sensor opposite the spinal segment so that a force impulse would be transmitted through the transducer in series with the spinal segment to be tested. An electronic wave form, characteristic of the combined resistance of the components in series, would be elicited upon the impact. Since all of the elements in series with the spinal segment, but not the spinal segment itself, were known or fixed to some standard, the variance of the system wave form would be attributed to the resistance of the spinal segment mobility relative to the adjacent spinal segments. This is the present state of the art and science.

While the present state of the art and science with the application of piezoelectric sensing devices has resulted in significant improvement over prior art, at least one additional variable exists: the angle of incidence of the device against the spinal segment. As the angle of incidence of the device against the spinal segment varies, the captured wave form will also vary to some degree upon impulse formation. The angle of incidence depends on the skill of the practitioner. Therefore, the accuracy of this device will also vary depending on the skill of the practitioner.

Highly skilled practitioners can be accurate in determining the correct angle of incidence but other practitioners may not be able to exactly match or reproduce angles selected by their peers. It is consistent with good laboratory practice that there be a given standard i.e. "the gold standard" that is the most accurate and precise standard available at the time of the present state of the art. Therefore, in the interest of good laboratory practice and in the interest of solving the problem of the potential inaccuracy of test results, the inventors hereof have conceived of a device which removes the greatest portion of the inaccuracies of spinal segment mobility test results.

Piezoelectric percussion testing is commonly used for testing materials with critical stress reliability needs i.e. microcircuits, aircraft frames and structural components, bridge materials etc. There are engineering standards for assessing the information contained in the wave form outputs from piezoelectric sensing systems used for structural materials testing. A search of literature and prior art fails to teach a method for gathering and interpreting the information trapped in a wave form generated as a result of piezoelectric sensing of percussion testing of human spinal segments.

While the present state of the art in spinal segment mobility testing has resulted in an improvement over prior art with the application of piezoelectric sensing devices and the logging of the amplitude of the wave form output from such piezoelectric sensing devices, there is much more complexity in the differing shapes of the wave forms elicited during the mobility testing of human spinal segments. Initial experiments and demonstrations have shown that there is useful information trapped in each wave form output of a piezoelectric sensor interposed in a percussion system for testing human spinal segment mobility. No method of capturing the mathematic representations of the wave form output from the percussive testing of human spinal segments and then manipulating and interpreting such mathematic representations so as to define the amount of segmental resistance or mobility and the condition and characteristics of such segmental resistance or mobility can be found in the prior art.

SUMMARY OF THE INVENTION

I provide a device for the measurement of spinal mobility which includes an impulse and sensing head capable of determining spinal segment mobility by applying a force impulse at an angle of incidence to a spinal segment and generating a wave form characteristic of spinal mobility. An inclinometer, disposed within the head, determines the angle of incidence of the head in contact with the spinal segment in at least one, preferably three, axis. Signal generating components are attached to the data acquisition circuitry, the inclinometer, and the head so that a signal corresponding to the angle of incidence of the head at substantially the same time that the head applies an impulse, will be captured by the data acquisition circuitry. Data acquisition circuitry also captures the wave form and a signal characteristic of the force impulse.

The impulse and sensing head includes a probe, a piezoelectric sensor firmly attached to the probe, an anvil firmly attached to the sensor, an electromagnetic coil and an armature. The armature is inserted without attachment into the electromagnetic coil and configured so that when the coil is energized, the armature is accelerated to impact the anvil and thereby produce the force impulse which travels through the piezoelectric sensor and causes the piezoelectric sensor to generate the wave form. A pressure sensor is attached to the head and configured so that when the probe is pressed against the spinal segment and reaches a predetermined pressure, the pressure sensor causes a release of a burst of current that energizes the electromagnetic coil. The pressure sensor is also attached to the signal generating components which output data, characteristic of the pressure of the probe in contact with the spinal segment, to the computer. The device is portable and hand-held.

The data acquisition circuitry includes a computer which has a screen. The angle of incidence in a three axis configuration is displayed on the screen. Information indicating the angle of incidence, the force impulse, the pressure of the probe and the wave form are stored in the computer. This information can be merged together, sorted, and logged for each patient. The computer can recall and print this information.

The device can be configured so that the head will only apply force impulse at a specific angle of incidence or within a specific range of angles of incidence. The device may also be constructed so that a signal, which may be visible or audible, is elicited if the angle of incidence does not fall within a specific range. Alternatively, the wave form may be blocked from data acquisition circuitry if the angle of incidence is not within a specific range.

The device can also be used to treat patients. The probe of the invention may oscillate by repetitively accelerating the armature and impact the anvil at a controlled frequency and a predetermined time period. The device would then be applied to a dysfunctional spinal segment for the purpose of improving joint mobility. Preferably, the frequency may be varied between approximately 4 and 12 hertz in increments of approximately 0.1 hertz.

I also provide a process of measuring spinal mobility which includes generating an impulse of a known force with a percussion source and transmitting the impulse through a piezoelectric sensor into an integument overlaying a spinal segment. This causes the piezoelectric sensor to generate a wave form having characteristics of the mobility of the spinal segment. The waveform is captured in a computer and the characteristics of the wave form are interpreted so as to make a correlation between mobility of the spinal segment and the characteristics of the wave form. The wave form may also be represented graphically on a computer screen or printed. The characteristics of the wave form are mathematic and visual. The graphic representation of the wave form is described statistically and mathematically. Ratios are calculated that mathematically describe the wave form offsets and asymmetries from an expected normal wave form. Ratios of each ¼ of the half wave form time from zero to peak versus time from peak back to zero and rise time versus fall time are determined and compared with the same ratios of an expected normal wave form. The resonant frequency of each spinal segment tested is calculated as a result of the wave form. A harmonic frequency is calculated of an oscillating percussion that would improve spinal mobility if applied to the spinal segment. The wave form is stored in the computer and displayed on the computer screen. The ratios are also stored in the computer and displayed graphically as numerical representations of the expected normal spinal mobility versus the spinal mobility of the spinal segment being tested. Charts are produced containing the ratios and the charts are used to determine a course of treatment. The results of the course of treatment are tracked against the expected normal spinal mobility. A file history of each patient is compiled which contains the mathematic and graphic representations and the ratio of that patient's spinal mobility. The mathematic and graphic representations in the ratios are transferred to a computer diskette and may be transferred to another computer.

BRIEF DESCRIPTION OF THE FIGURES

FIG. 8 shows a computer screen displaying a summary table of all the information from FIGS. 3 and 4 as displayed in FIG. 7.

DESCRIPTION OF THE PREFERRED EMBODIMENT

Figure 1:
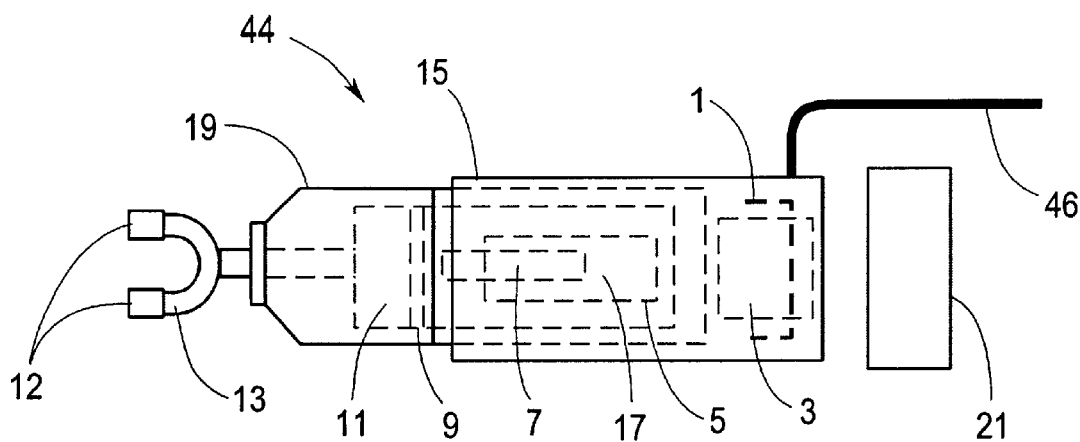
FIG. 1 is a cross-sectional side view of an impulse and sensing head.

The device for measurement of spinal mobility is portable and hand-held and includes an elongated generally cylindrical housing 15 which has an insert 19 that tapers to form a generally conical configuration at one end as shown in FIG. 1. The other end of the housing 15 is provided with a cylindrical closed end 21. The housing 15 and the closed end 21 may be separately connected by a screw threaded connection to provide access into the interior of the housing 15 and to separate the components of the invention for repair, replacement and the like. After housing 15 is unscrewed from closed end 21, it can slide back and insert 19 can also be unscrewed from the housing 15.

A probe 13 is located at the forward end 19 of the housing 15 and includes cushioned tips 12 for contacting the spinal segment to be measured. The probe 13 may be constructed of a rigid material such as metal, plastic, or the like. The probe 13 screws into or frictionally inserts into the piezoelectric sensor 11. Different shaped probes 13 may be used depending on if the apparatus is being used to measure spinal mobility or is being used for therapeutic purposes to improve joint mobility.

Within the housing 15 is a solenoid assembly 17. The assembly 17 includes an electromagnetic coil 5 and an armature 7 longitudinally reciprocally mounted without attachment within the coil 5. The armature 7 is configured so that the end of the armature 7 will impact against the anvil 9 when the electromagnetic coil 5 is energized. The anvil 9 is affixed to one side of a piezoelectric sensor 11. The impact produces a force impulse which travels through the piezoelectric sensor 11 and causes the piezoelectric sensor 11 to generate a wave form. When any one of the various probes is placed against the integument of a patient, the other end of the probe 13 resides firmly against the piezoelectric sensor 11 which in turn resides firmly against the anvil 9. A pressure sensor 3 that resides within the housing 15 is interposed between the closed end 21 of the housing 15 and the solenoid 17. The pressure sensor 3, works in concert with each of the other components so that upon reaching a point that corresponds to a predetermined pressure against the integument of a human subject, the pressure sensor 3 causes the release of a burst of current that energizes the electromagnetic coil 5 such that the armature 7 is accelerated to impact with the anvil 9. The pressure sensor may be comprised of a load cell. The impact of said armature 7 against the anvil 9 produces a force impulse which travels directionally, in a continuum with the direction of the armature 7 at impact, through the piezoelectric sensor 11 while at the same time being influenced by the resistance placed upon the piezoelectric sensor 11 by the probe 13 which is contact with the patient. The kinetic energy at the point of impact causes the piezoelectric sensor 11 to emit an electronic wave form which is characteristic of all of the elements of the electromechanical system on one side of the sensor opposed by all of the human elements on the other side of the sensor. The wave form is captured by data acquisition circuitry within a computer and retained therein for wave form analysis by the application of certain algorithms. Preferably, the power supply is in the CPU. Cord 46 connects the device to the power supply. Alternatively, the current may be supplied through an electrical cord that may be plugged into a suitable electrical outlet or the like which extends into the housing.

The mass of the armature 7 is substantially equal to the mass of the anvil 9 so that when the armature 7 strikes the anvil 9 it transfers the energy of the armature 7 to the patient through the cushioned probe 13. The initial positions of the coil and the probe 13 are fixed so that the energy of the system can only be varied by varying velocity of the armature 7 at the point of impact with the anvil 9. The velocity of the armature 7 can be varied by varying the force with which it is accelerated into the electromagnetic coil 5 which is proportional to the current flowing into the coils of the solenoid 17 which in turn is proportional to the voltage. The triggering point at which the solenoid 17 is actuated can be varied by the relative movement pressure of the housing 15 inwardly in relation to the solenoid 17 and the probe 13 so that when the preset pressure has been matched an electrical circuit is completed to the electromagnetic coil 5.

A single, or preferably, multi-axis inclinometer, disposed within the head 44, will sense the angle of incidence of the probe 13 in contact with the spinal segment being tested simultaneously with the formation of the wave form. The inclinometer 1 is connected by hard-wiring or telemetry to the data acquisition circuitry. A signal corresponding to the angle of incidence will be captured by the data acquisition circuitry of the computer and retained for display on the computer screen.

In the preferred embodiment, the device herein described may be used for therapeutic as well as analytical applications. For example, after an analysis is completed, a health care practitioner may use oscillating percussion for treatment of joint dysfunction. This may be accomplished by repetitively accelerating the said armature 7 to impact the anvil 9 thereby causing the probe 13 to oscillate. The percussive force of the probe 13 should be applied to a dysfunctional spinal segment for the purpose of improving joint mobility. This may be done at a controlled impulse frequency of repetitive force impulses at a predetermined time period or a time period selected by the computer as a result of software algorithms. In the preferred embodiment, the frequency of percussion is varied between 4 and 12 Hertz in increments of 0.1 Hertz. Because there is an inclinometer 1 within the therapy delivery head 44, precise angles of therapy may be applied to the patient and documented for future reference. X-ray imaging may also be used in conjunction with the invention herein claimed for accurate estimation of the angle of incidence for therapeutic purposes.

Data characteristic of the angle of incidence, pressure of the probe 13 on the patient and the force impulse are permanently stored in computer memory for each spinal segment tested, inclusive of all of the tests performed on a given patient during a given session so that such information may be combined with the test interpretation as derived from the analysis of the elicited wave form for each segment tested. A basis or "base line" is provided for comparison to the test angle of incidence so that those test angles can be matched during the performance of additional testing. The stored angle of incidence information along with the test data analysis for each patient session can be recalled and printed. Any part or, if practical, all of the test history of any patient can be combined for inclusion on one or more computer diskettes so as to enable transfer of the records to any other practitioner so equipped to use the information in the furtherance of the care of the patient. Because the test angle is recorded and permanently stored, another doctor giving a second opinion can use the same angle for testing. Therefore, the results of tests performed by different doctors will be more uniform.

Figure 2:
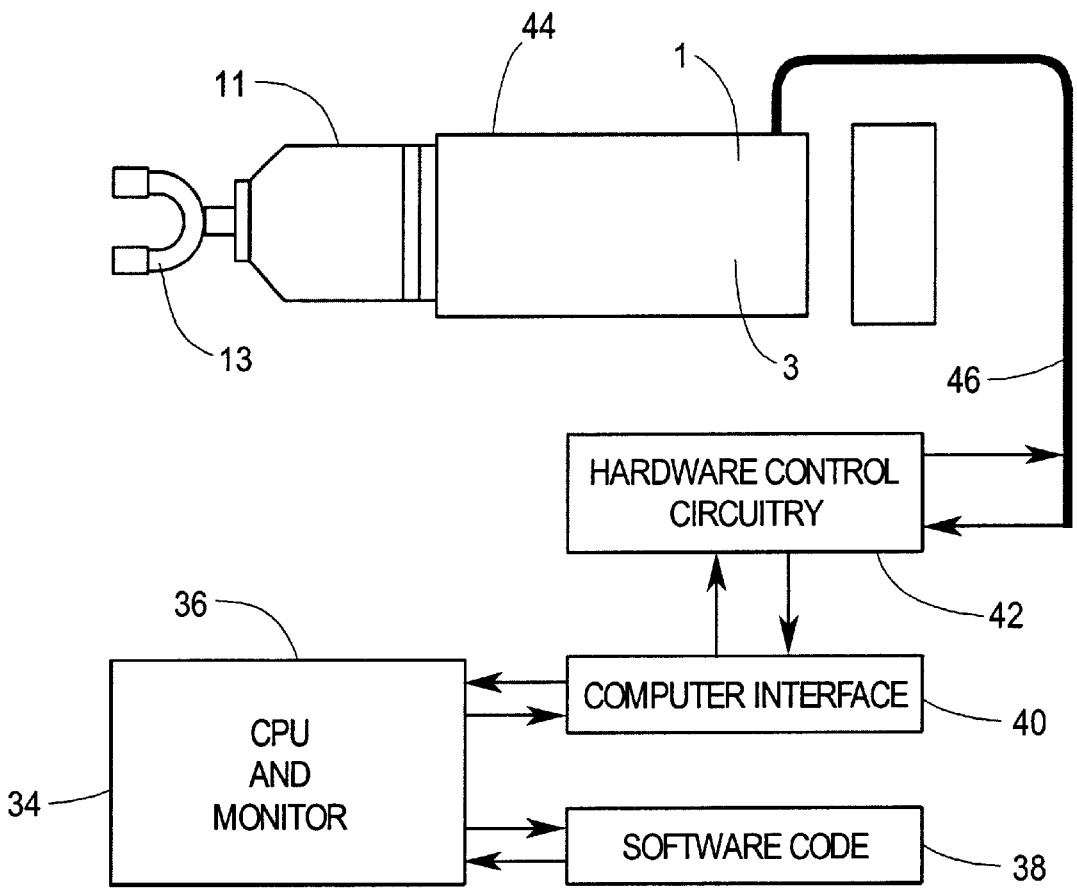
FIG. 2 is a schematic diagram showing the hardware components of the device used to create and capture the wave form.

FIG. 2 is a block diagram of the architecture of the computer and piezoelectric impulse and sensing head 44. In one embodiment of the invention, the electromechanical impulse and sensing head 44 is activated and controlled with computer software code 38 written onto a CPU 34 that communicates through an interface 40 to hardware control circuitry 42 and to the impulse and sensing head 44. Signals from the sensors within the impulse and sensing head 44 travel to the hardware control circuitry 42 for conditioning and transmittal through the computer interface 40 circuitry to the CPU 34. Software code 38 is used to control and direct all signals between the electromechanical component and the computer. All relevant information generated by the process is stored and may be recalled onto the monitor 36 or printed as required.

The resulting wave form is sinusoidal and will be influenced by such things as joint mobility or resistance to mobility, fascia tension, muscle tonicity, connective tissue resiliency or inertia, local edema etc. Each such wave form may be characterized mathematically by logging the peak amplitude, peak time, rise time, fall time, and slue rate. The mathematic values of the data logged will facilitate the calculation of frequency response and certain ratios that will mathematically define the wave form characteristics. By analyzing the mathematics of the wave form characteristics, certain assumptions can be made as to the functional characteristics of the joint and of the tissue condition surrounding the spinal motion segment being tested.

As the data are collected and logged and after all of the pertinent mathematic calculations are made, a graphic display of the wave form may be presented on a display device i.e. a computer monitor. In addition to the graphic display, the pertinent data and derived ratios may be displayed for assessment by the user of the equipment. The user will be one trained in the interpretation of the wave form shape and interpretation of the logged and derived mathematic information. The graphic displays plus all of the mathematic information as a result of spinal segment percussion testing may be stored and recalled whenever deemed necessary. As the data base grows and expands, clinical assumptions will yield to statistically valid probabilities and predictive diagnoses. A permanent record of each test of each patient may be stored and recalled as necessary. It may also be copied to a computer diskette so that it can be transferred to another computer.

As each wave form is recovered from the piezoelectric sensor, several things become apparent. The amplitude of the wave form is important because as spinal segment resistance increases, the test wave form amplitude increases. Therefore, in FIG. 3 a simple bar chart 67 is used for the expression of wave form peak amplitude. A statistical analysis (mean and standard deviation) of the amplitudes is included. Standard deviation may be set at one, two or three sigma and is expressed by a horizontal line on bar chart 69. The shape of the wave is an important piece of information. The expression of a ½ wave form 71 in a graphic display of the wave form shape for all spinal segments. A composite of all 7 Cervical, 12 Thoracic, or 10 Lumbosacral wave forms 73 is expressed before treatment and after treatment.

Figure 3:
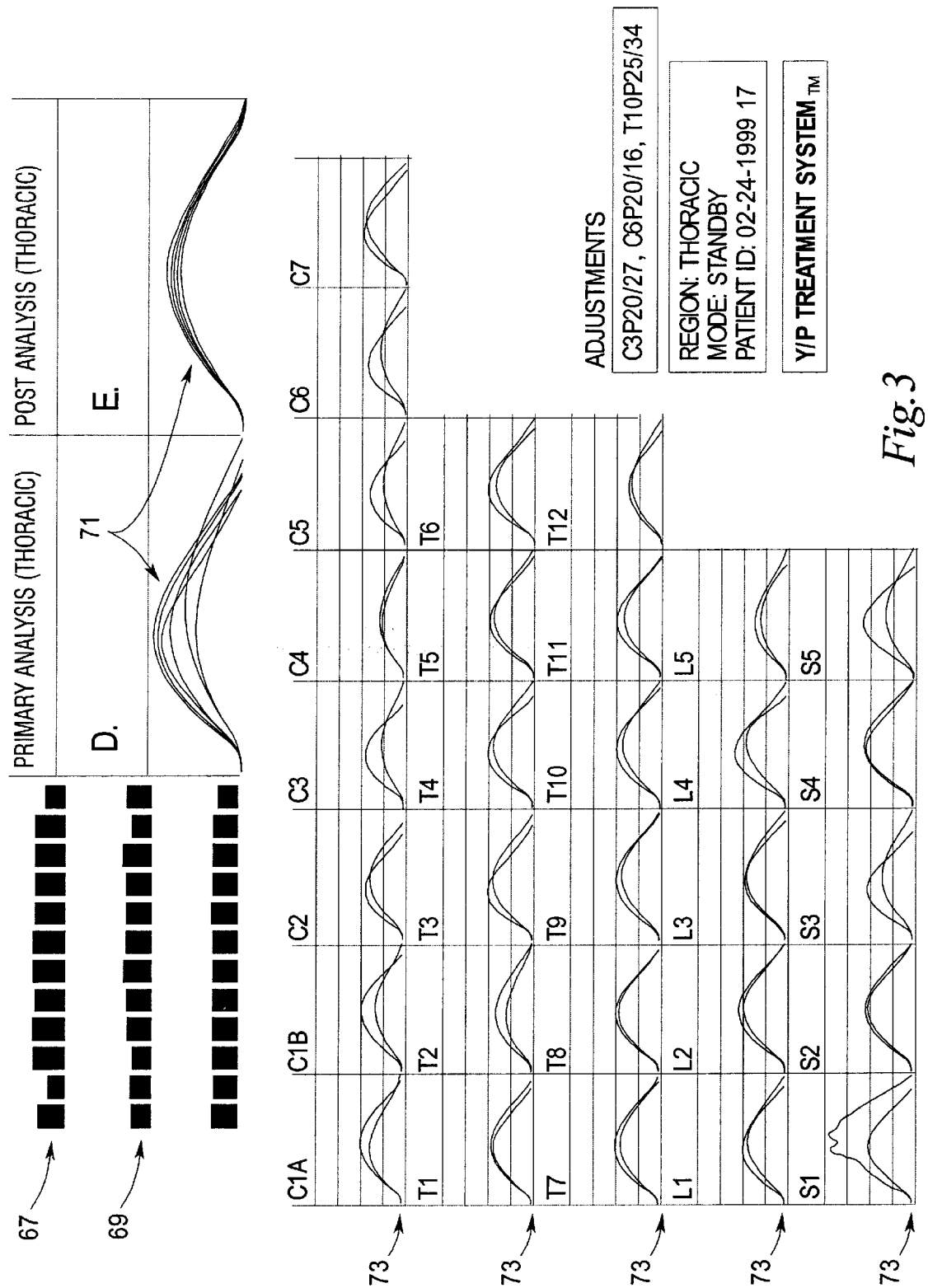
FIG. 3 depicts the thoracic analysis and treatment computer screen in the preferred embodiment.
Figure 5:
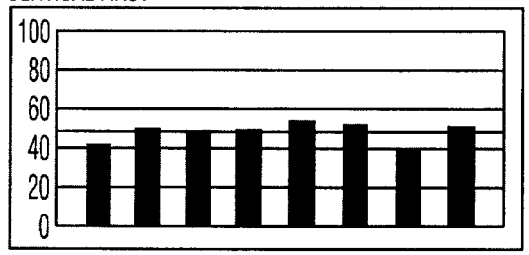
FIG. 5 shows a computer screen displaying a summary of the peak amplitudes taken from the wave forms on FIG. 3.
Figure 5:
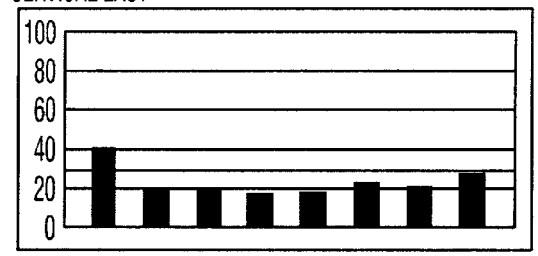
Figure 5:
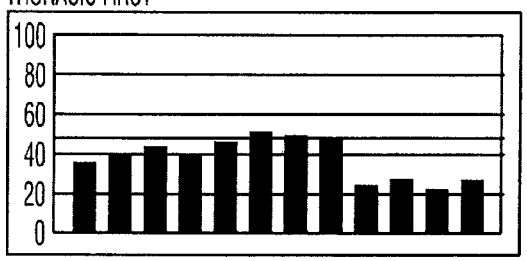
Figure 5:
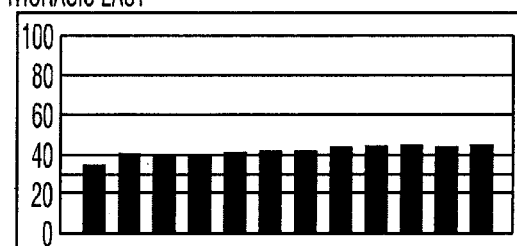
Figure 5:
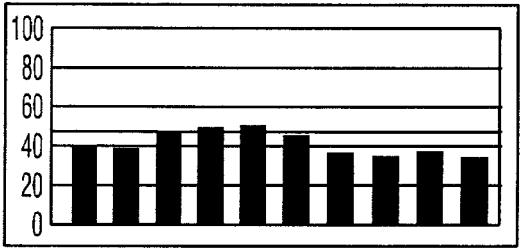
Figure 5:
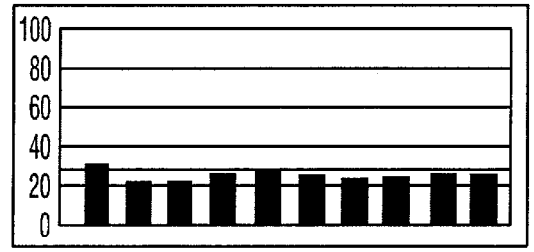
Figure 6:
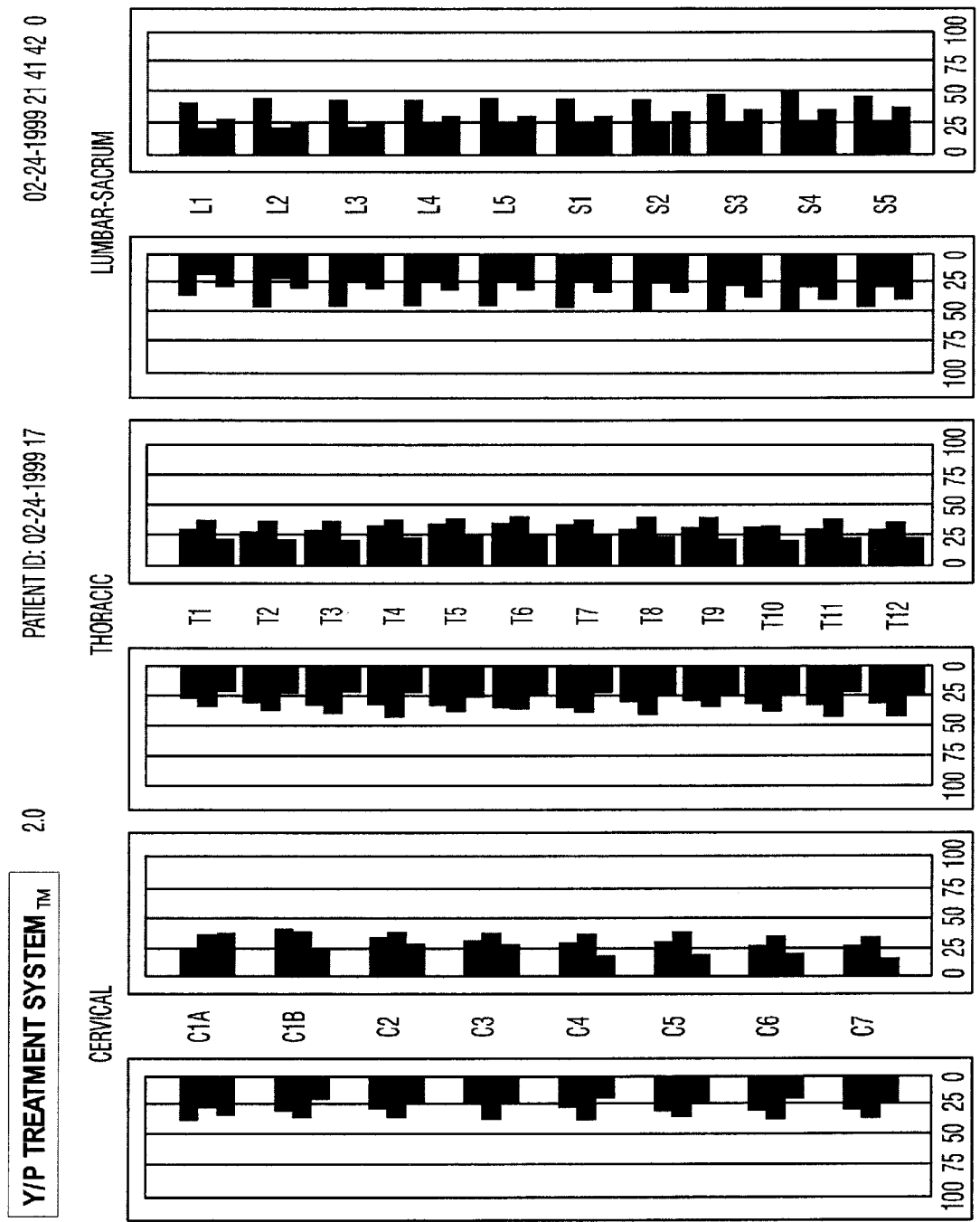
FIG. 6 shows a computer screen displaying a summary of the peak amplitudes taken from the wave forms in FIG. 4.

There are three computer screens that would appear similar to FIG. 3, one for Cervical analysis and treatment, one for Thoracic analysis and treatment, and one for Lumbosacral analysis and treatment. The composite of all wave forms 73 will be the same on all three screens. There will be three additional screens, like the one shown in FIG. 4, for the Lateral analysis and treatment information. FIG. 5 is a summary of the peak amplitudes taken from the wave forms on FIG. 3. FIG. 6 is the summary of the peak amplitudes taken from the wave forms in FIG. 4.

Figure 4:
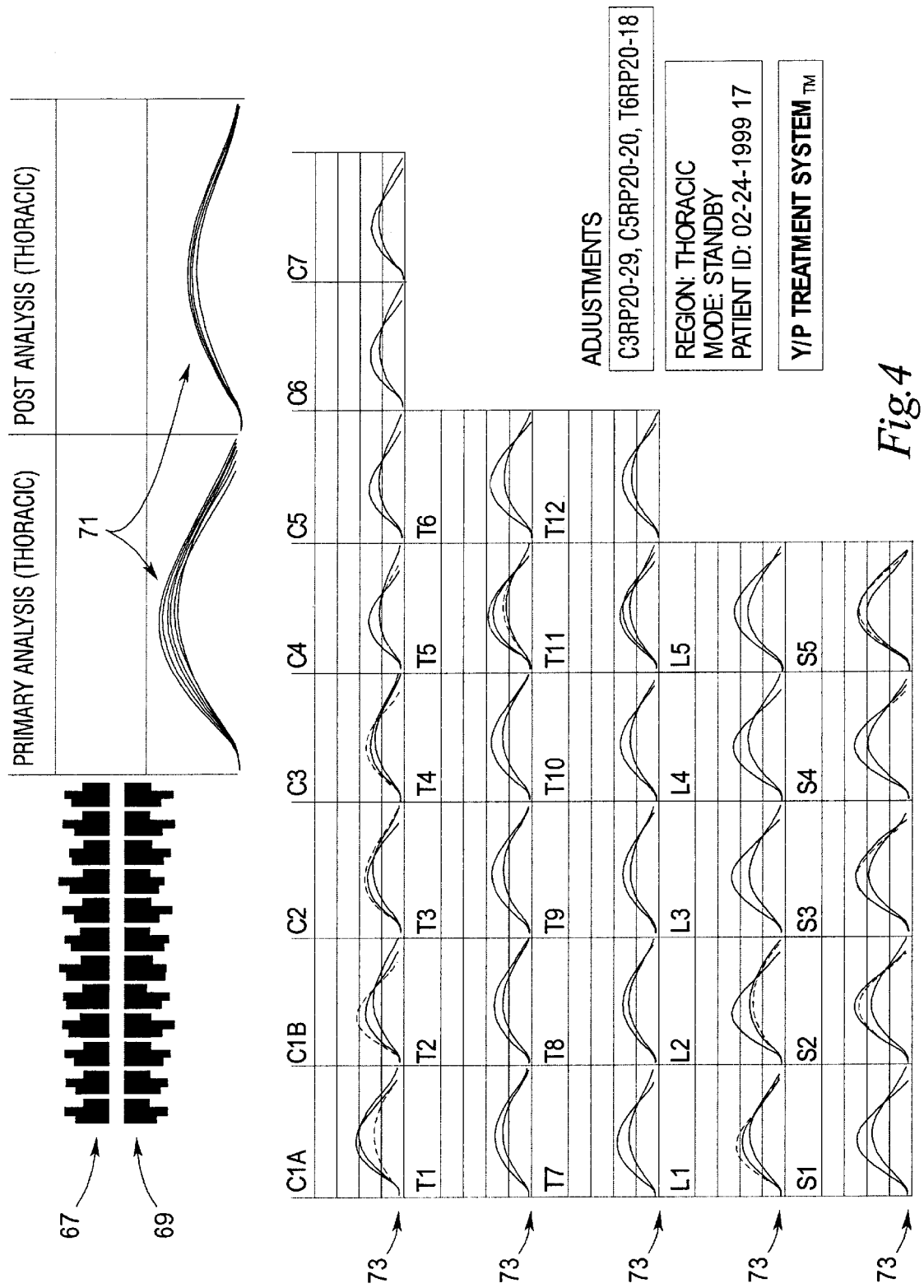
FIG. 4 depicts the lateral analysis and treatment computer screen in the preferred embodiment.
Figure 7:
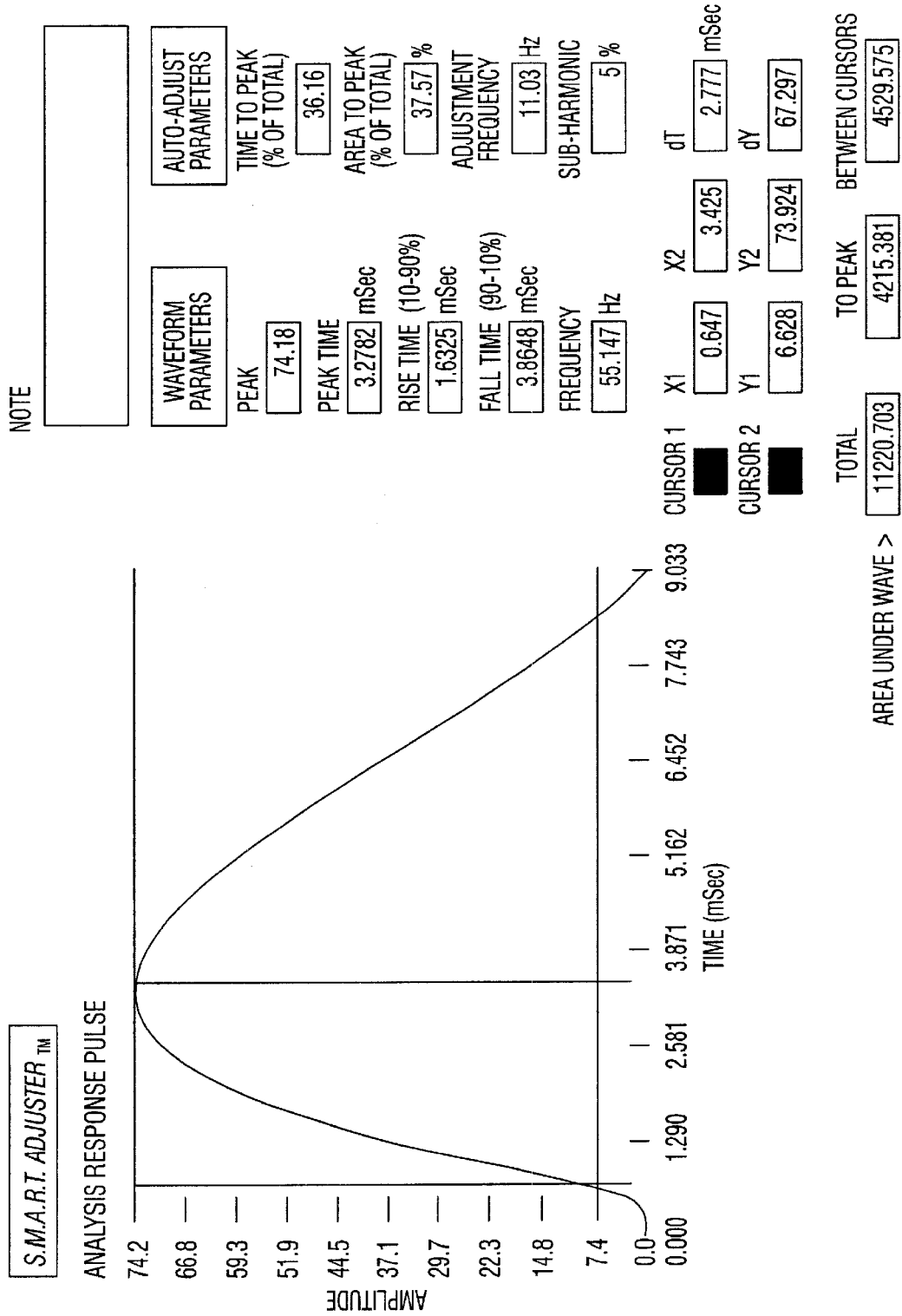
FIG. 7 shows a computer screen depicting a wave form which has derived information from each of the screens shown in FIGS. 3 and 4.
Figure 9:
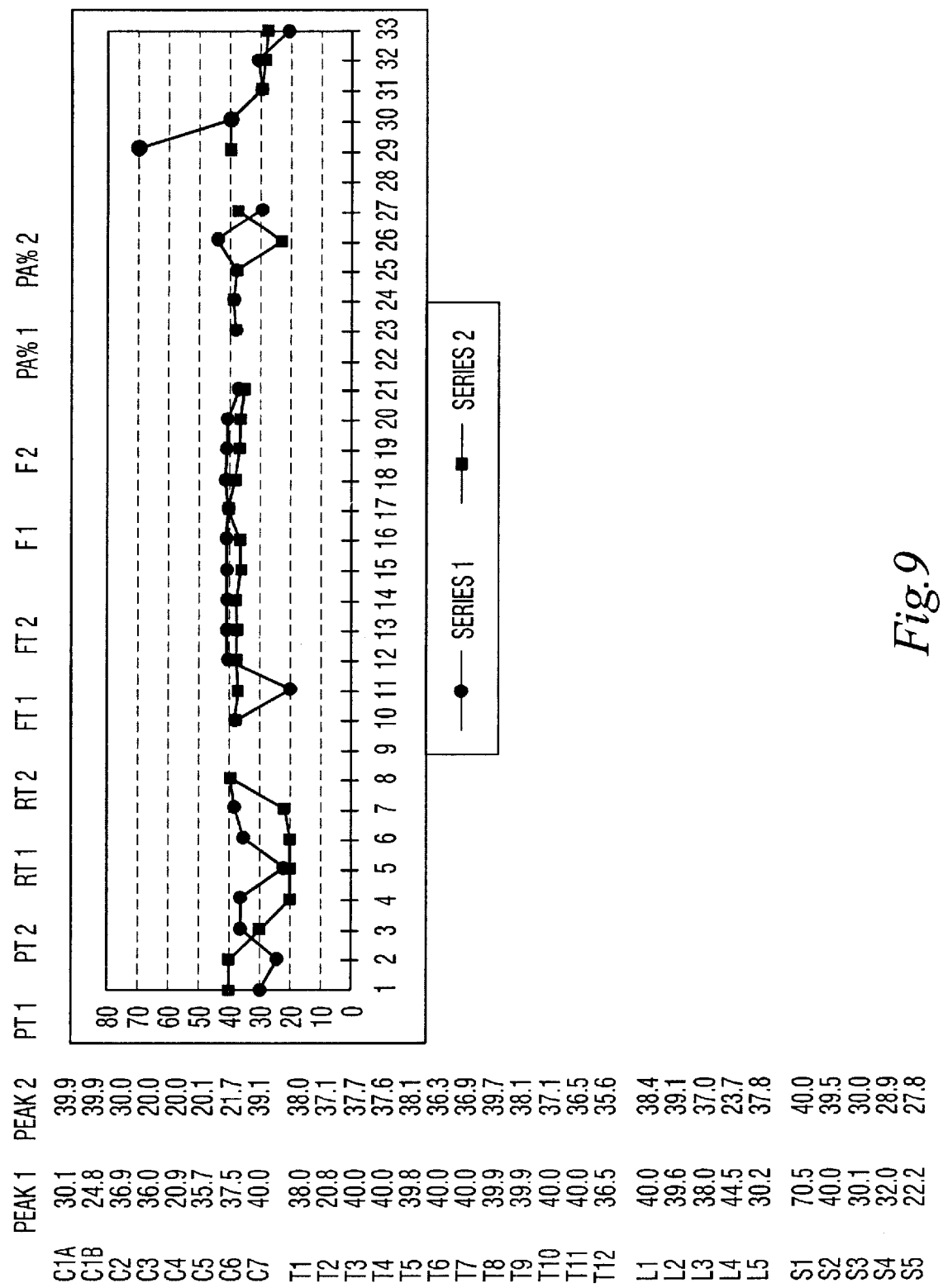
FIGS. 9 through 12 are a sample of charts that may be produced so that data may be presented in an informational format for comparison.
Figure 10:
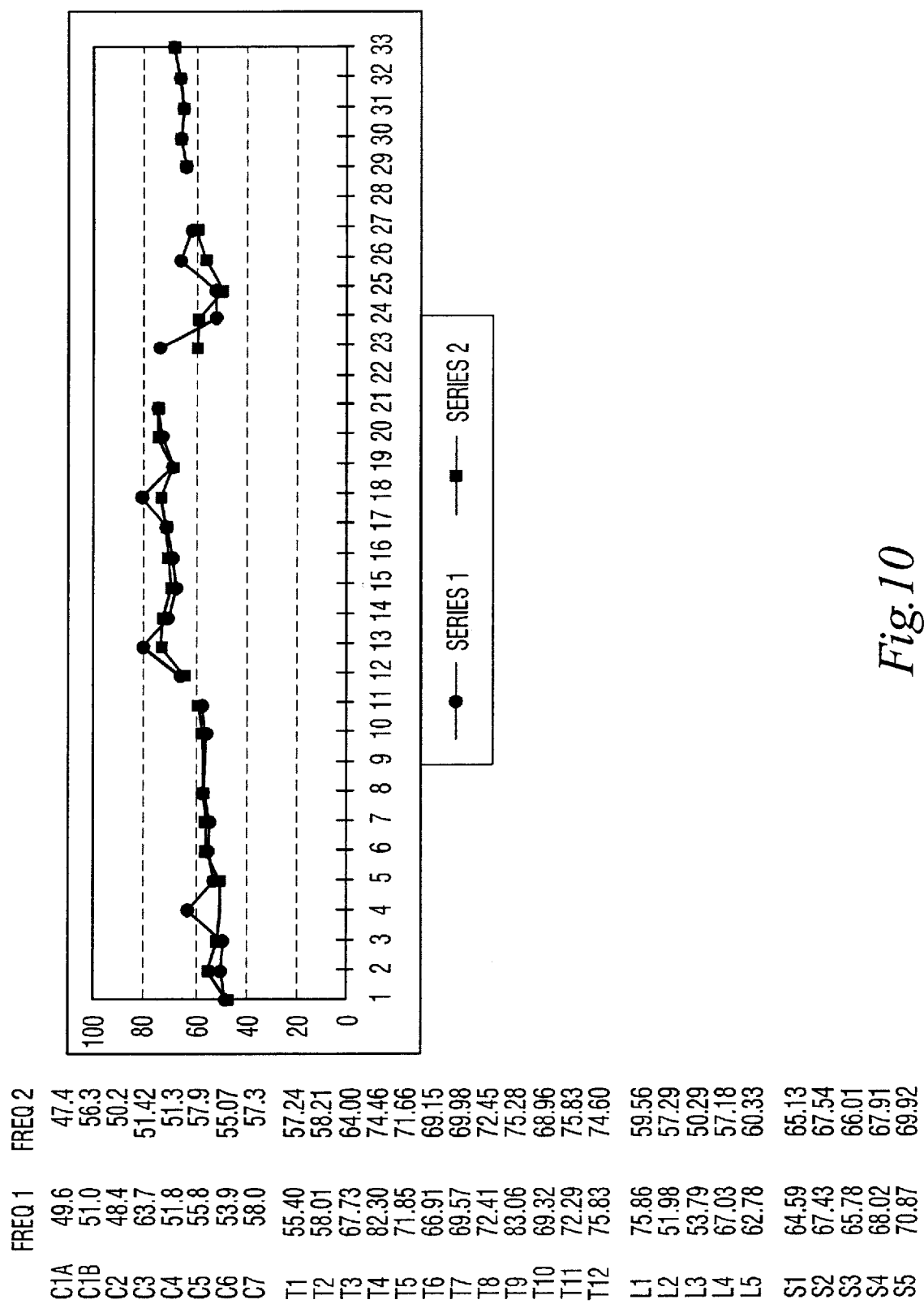
Figure 11:
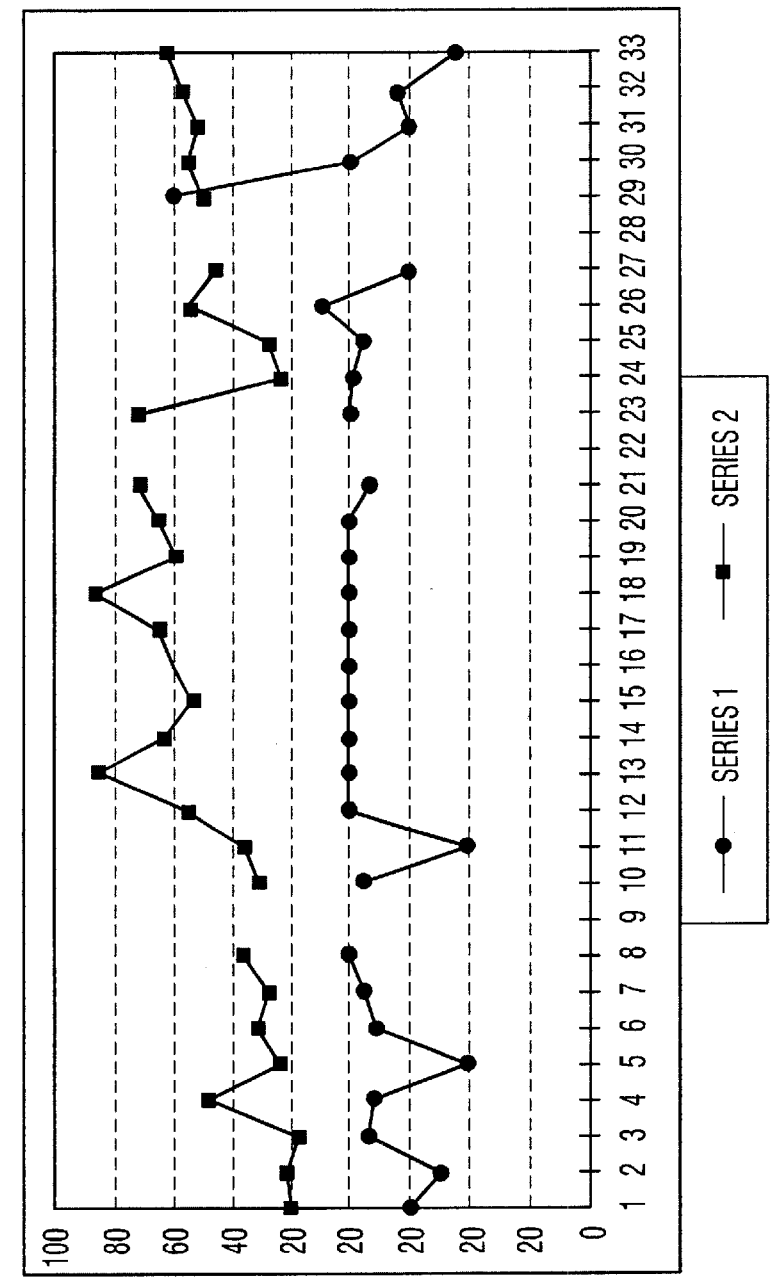
Figure 12:
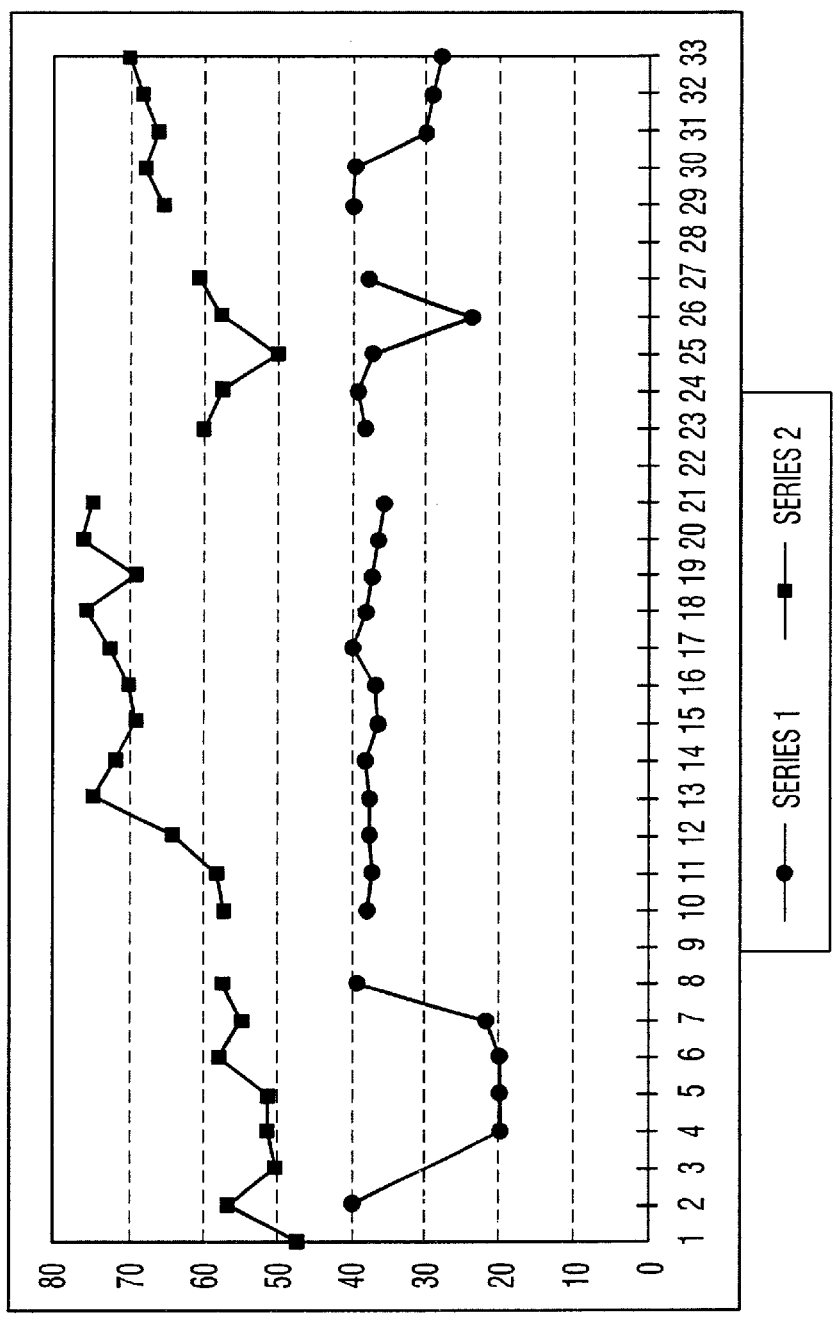

Each of the wave forms represented on FIG. 3 and FIG. 4 are analyzed for Peak Amplitude, Peak Time, Rise Time, Fall Time, Frequency (Hertz), Time (%) to Peak and Area (%) to Peak. The derived information is displayed as shown on FIG. 7 along with some calculated factors that are also shown. From the information derived and calculated, a summary table, in FIG. 8, showing all of the derived values may be produced. From the data on FIG. 8, charts may be produced so that the data may be presented in an informational format for comparisons. A sample of these charts is shown as FIGS. 9 through 13. Normal values can be compiled and charted and used to determine normal versus aberrant joint motion and for comparison to the pre-treatment and post-treatment charts.

Using the information presented as herein described, a practitioner may determine treatment protocol and track progress with objectivity. The practitioner may calculate the resonant frequency of the spinal motion segment as a result of the wave form duration in milliseconds and use an algorithm to calculate a harmonic frequency that would be used during patient therapy to control the oscillating percussion used for joint mobility treatment. A history of patient analysis and treatment may be compiled and used for discussion of patient's condition and progress as well as justification for continuing treatment and rehabilitation. Results of rehabilitation may also be used for demonstration of patient cooperation and compliance to a prescribed exercise and rehabilitation program.

Although I have shown the present preferred embodiment of my device for the measurement of spinal mobility, it should be distinctly understood that the invention is not limited thereto, but may be variously embodied within the scope of the following claims.

We claim:

1. A device for the measurement of spinal mobility comprising:

(a) a probe configured to contact a spinal segment at an angle of incidence;

(b) a piezoelectric sensor firmly attached to the probe;

(c) an anvil firmly attached to the sensor;

(d) an electromagnetic coil;

(e) an armature which is inserted without attachment in the electromagnetic coil and configured so that when the coil is energized, the armature is accelerated to impact the anvil and thereby produce a force impulse which travels through the piezoelectric sensor and the probe to the spinal segment and causes the piezoelectric sensor to generate a wave form characteristic of spinal mobility; and (f) an inclinometer configured so that the inclinometer can determine the angle of incidence of the probe in contact with the spinal segment.

2. A device for the measurement of spinal mobility comprising:

(a) an impulse and sensing head capable of determining spinal segment mobility by applying a force impulse, at an angle of incidence, to a spinal segment, and generating a wave form characteristic of spinal mobility;

(b) an inclinometer disposed within the head, the inclinometer being able to determine the angle of incidence in at least one axis;

(c) data acquisition circuitry which captures the wave form; and (d) signal generating components attached to the data acquisition circuitry, the inclinometer, and the head for generating a signal corresponding to the angle of incidence of the head.

3. The device for measuring spinal mobility in claim 2 wherein the impulse and sensing head includes:

(1) a probe configured to contact a spinal segment;

(2) a piezoelectric sensor firmly attached to the probe;

(3) an anvil firmly attached to the sensor;

(4) an electromagnetic coil; and (5) an armature which is inserted without attachment in the electromagnetic coil and configured so that when the coil is energized, the armature is accelerated to impact the anvil and thereby produce the force impulse which travels through the piezoelectric sensor and causes the piezoelectric sensor to generate the wave form.

4. The device for measuring spinal mobility in claim 2 further comprising a pressure sensor attached to the head and configured so that when the probe is being pressed against a spinal segment and reaches a predetermined pressure, the pressure sensor causes a release of a burst of current that energizes the electromagnetic coil.

5. The device for the measurement of spinal mobility in claim 4 wherein the inclinometer is able to determine the angle of incidence in 3 axis.

6. The device for the measurement of spinal mobility in claim 5 wherein the device is portable.

7. The device for the measurement of spinal mobility in claim 6 wherein the device is hand held.

8. The device for the measurement of spinal mobility in claim 7 wherein the data acquisition circuitry includes a computer having a screen, the computer being configured to display the angle of incidence in at least one axis on the screen.

9. The device for the measurement of spinal mobility in claim 8 wherein data indicating the angle of incidence in at least one axis is stored in the computer.

10. The device for the measurement of spinal mobility in claim 9 wherein the wave form is stored in the computer.

11. The device for the measurement of spinal mobility in claim 10 wherein the data indicating the angle of incidence is merged with the wave form.

12. The device for the measurement of spinal mobility in claim 11 wherein the pressure sensor is attached to the signal generating components which output data, characteristic of the pressure of the probe in contact with the spinal segment, to the computer, and the computer stores the data.

13. The device for the measurement of spinal mobility in claim 12 wherein the data characteristic of the pressure of the probe is merged with the data indicating the angle of incidence in at least one axis.

14. The device for the measurement of spinal mobility in claim 13 wherein the signal generating components output data characteristic of the force impulse to the computer, and the computer stores the data.

15. The device for the measurement of spinal mobility in claim 14 wherein the data characteristic of the force impulse is merged with the data indicating the angle of incidence in at least one axis.

16. The device for the measurement of spinal mobility in claim 15 wherein the data indicating the angle of incidence in at least one axis, the data characteristic of the pressure of the probe, the data characteristic of the force impulse and the wave form are sorted and logged.

17. The device for the measurement of spinal mobility in claim 16 wherein the data indicating the angle of incidence in at least one axis, the data characteristic of the pressure of the probe, the data characteristic of the force impulse and the wave form are sorted and logged for each patient.

18. The device for the measurement of spinal mobility in claim 17 wherein the computer can recall and print the wave form, the data indicating the angle of incidence in at least one axis, the data characteristic of the pressure of the probe, and the data characteristic of the force impulse.

19. The device for the measurement of spinal mobility in claim 18 wherein the head oscillates.

20. The device for the measurement of spinal mobility in claim 19 wherein the armature is repetitively accelerated to impact the anvil thereby oscillating the head.

21. The device for the measurement of spinal mobility in claim 20 wherein the head oscillates at a controlled frequency.

22. The device for the measurement of spinal mobility in claim 21 wherein the frequency may be varied between approximately four and twelve Hertz in increments of approximately 0.1 Hertz.

23. The device for the measurement of spinal mobility in claim 22 wherein the head oscillates at a predetermined time period.

24. The device for the measurement of spinal mobility in claim 23 wherein the head will apply a force impulse only at a specific angle of incidence.

25. The device for the measurement of spinal mobility in claim 24 wherein the head will apply a force impulse only if the angle of incidence falls within a specific range.

26. The device for the measurement of spinal mobility in claim 25 further comprising a signal which is elicited if the angle of incidence is not within the range.

27. The device for the measurement of spinal mobility in claim 23 further comprising a signal which is elicited if the angle of incidence does not fall within a specific range.

28. The device for the measurement of spinal mobility in claim 26 or 27 wherein the signal is visible.

29. The device for the measurement of spinal mobility in claim 26 or 27 wherein the signal is audible.

30. The device for the measurement of spinal mobility in claim 23 wherein the wave form is blocked from the data acquisition circuitry if the angle of incidence is not within a specific range.

31. The device for the measurement of spinal mobility in claim 30 wherein the angle of incidence in at least one axis may be viewed on the computer screen before the wave form is elicited.

32. A process of measuring spinal mobility which comprises:
 (a) generating an impulse of a known force with a percussion source;
 (b) transmitting the impulse through a piezoelectric sensor into an integument overlaying a spinal segment so that the piezoelectric sensor generates a wave form having characteristics of the mobility of the spinal segment;
 (c) capturing the wave form in a computer; and
 (d) interpreting the characteristics of the wave form so as to make a correlation between mobility of the spinal segment and the characteristics of the wave form, wherein an inclinometer is connected to said piezoelectric sensor.

33. A process of measuring spinal mobility as recited in claim 32, wherein said inclinometer is configured to determine the angle of incidence of said piezoelectric sensor in contact with said spinal segment.

34. A process of measuring spinal mobility, comprising:
 (a) generating an impulse of known force with a percussive source;
 (b) transmitting said impulse through a sensor into an integument overlaying a spinal segment so that said sensor generates a wave form;
 (c) measuring the angle of incidence of said sensor in contact with said integument;
 (d) capturing said wave form; and
 (e) interpreting the characteristics of said wave form.

35. A device for treating spinal ailments, comprising:
 (a) a probe configured to contact a spinal segment at an angle of incidence;
 (b) a sensor attached to said probe;
 (c) an impulse source attached to said sensor; and (d) an inclinometer configured to determine the angle of incidence of said probe in contact with said spinal segment.

36. A device for treating spinal ailments comprising:
   (a) a probe configured to contact a spinal segment at an angle of incidence;
   (b) a piezoelectric sensor attached to said probe;
   (c) an anvil attached to said sensor;
   (d) an electromagnetic coil;
   (e) an armature carried within said electromagnetic coil and configured so that when said coil is energized, said armature is accelerated to impact said anvil and thereby produce a force impulse which travels through said piezoelectric sensor and said probe to said spinal segment and causes said piezoelectric sensor to generate a wave form characteristic of spinal mobility; and
   (f) an inclinometer configured so that said inclinometer can determine the angle of incidence of said probe in contact with said spinal segment when said wave form is generated.

37. A device for treating spinal aliments comprising:
   (a) an impulse and sensing head for applying a force impulse, at an angle of incidence, to a spinal segment, and for generating a wave form;
   (b) an inclinometer disposed within said head, said inclinometer for determining the angle of incidence along at least one axis;
   (c) data acquistion circuitry for capturing said wave form; and
   (d) signal generating components for generating a signal corresponding to the angle of incidence of said head when said head applies an impulse.

38. A device, comprising:
   (a) a probe configured to contact a spinal segment at an angle of incidence;
   (b) a sensor attached to said probe;
   (c) an impulse source attached to said sensor; and
   (d) an inclinometer configured to determine the angle of incidence of said probe in contact with said spinal segment.

\* \* \* \* \*